United States Patent
Laikind (10) Patent No.: US 10,603,680 B2
(45) Date of Patent: Mar. 31, 2020

(54) PERSONAL COOLING MISTING SYSTEM

(71) Applicant: Ronald Brian Laikind, Scottsdale, AZ (US)

(72) Inventor: Ronald Brian Laikind, Scottsdale, AZ (US)

(*) Notice: Subject to any disclaimer, the term of this patent is extended or adjusted under 35 U.S.C. 154(b) by 0 days.

(21) Appl. No.: 15/723,829

(22) Filed: Oct. 3, 2017

(65) Prior Publication Data
US 2019/0001354 A1    Jan. 3, 2019

Related U.S. Application Data

(60) Provisional application No. 62/528,283, filed on Jul. 3, 2017.

(51) Int. Cl.
| | | |
|---|---|---|
| B05B 7/00 | (2006.01) |
| B05B 7/24 | (2006.01) |
| B05B 1/02 | (2006.01) |
| B05B 12/12 | (2006.01) |
| B05B 12/06 | (2006.01) |
| B05B 12/00 | (2018.01) |
| F24F 5/00 | (2006.01) |
| A45B 23/00 | (2006.01) |
| A61F 7/00 | (2006.01) |
| B05B 9/08 | (2006.01) |

(52) U.S. Cl.
CPC ............ *B05B 7/2475* (2013.01); *A45B 23/00* (2013.01); *A61F 7/00* (2013.01); *B05B 1/02* (2013.01); *B05B 9/085* (2013.01); *B05B 12/006* (2013.01); *B05B 12/06* (2013.01); *B05B 12/12* (2013.01); *F24F 5/0035* (2013.01); *A45B 2200/1045* (2013.01); *A61F 2007/0063* (2013.01); *A61F 2007/0078* (2013.01); *A61F 2007/0093* (2013.01); *A61F 2007/0094* (2013.01); *A61F 2007/0095* (2013.01)

(58) Field of Classification Search
CPC ..... B05B 9/0426; B05B 9/085; B05B 9/0861; B05B 9/0866; B05B 9/0888
USPC .......................... 239/33, 333, 338, 436, 302
See application file for complete search history.

(56) References Cited

U.S. PATENT DOCUMENTS

| | | | | |
|---|---|---|---|---|
| 1,555,467 A | * | 9/1925 | Graham ................. | A01G 25/14 137/585 |
| 3,389,079 A | * | 6/1968 | Litt .......................... | C02F 1/001 210/650 |

(Continued)

*Primary Examiner* — Viet Le
(74) *Attorney, Agent, or Firm* — Thomas I. Rozsa (57) ABSTRACT

The personal cooling misting system disclosed provides for a wearable fluid reservoir to contain a volume of misting fluid, and an electrically operated pump proximate to the reservoir to pump the misting fluid from the reservoir to a misting head. The misting head facilitates atomizing the misting fluid. The system further provides for feed tubing to direct the misting fluid from the reservoir to the pump, and distributive tubing to direct the misting fluid from the pump to the misting head. The system also includes a pump control to control at least one of a pressure and a flow rate of the misting fluid through at least one of the feed tubing and distributive tubing, and the system includes a programmable circuit board to facilitate system control via the pump control, as well as directing to the pump control a misting distribution pattern for at least one of a consistent or intermittent misting pattern.

20 Claims, 4 Drawing Sheets

(56) References Cited

U.S. PATENT DOCUMENTS

| | | | | |
|---|---|---|---|---|
| 4,801,088 A * | 1/1989 | Baker | B05B 9/0861 | 222/175 |
| 4,807,813 A * | 2/1989 | Coleman | A63H 33/28 | 222/175 |
| 4,815,635 A * | 3/1989 | Porter | B62J 11/00 | 222/136 |
| 4,921,143 A * | 5/1990 | Billet | B67D 1/04 | 222/175 |
| 5,045,195 A * | 9/1991 | Spangrud | C02F 1/002 | 210/266 |
| 5,060,833 A * | 10/1991 | Edison | A45F 3/16 | 215/388 |
| 5,129,584 A * | 7/1992 | Ridenour | B05B 1/3026 | 239/579 |
| 5,154,317 A * | 10/1992 | Roppolo, III | B05B 9/007 | 222/331 |
| 5,201,442 A * | 4/1993 | Bakalian | A45F 3/16 | 222/608 |
| 5,304,035 A * | 4/1994 | Carter | F04D 25/084 | 224/258 |
| 5,326,124 A * | 7/1994 | Allemang | B62J 11/00 | 222/610 |
| 5,390,858 A * | 2/1995 | Watson | A01G 25/095 | 239/242 |
| 5,478,015 A * | 12/1995 | Black | B05B 9/0877 | 222/175 |
| 5,595,325 A * | 1/1997 | Leres | B67D 3/00 | 222/135 |
| 5,752,661 A * | 5/1998 | Lewis | B05B 9/0861 | 222/175 |
| 5,799,873 A * | 9/1998 | Lau | B05B 9/0805 | 239/33 |
| 6,010,034 A * | 1/2000 | Walthers | A47G 19/2266 | 222/129 |
| 6,161,777 A * | 12/2000 | Carter | A45F 3/16 | 239/222.11 |
| 6,189,805 B1 * | 2/2001 | West | B05B 1/20 | 239/152 |
| 6,189,811 B1 * | 2/2001 | Rudy | F04B 17/006 | 239/375 |
| 6,213,358 B1 * | 4/2001 | Libit | B05B 11/0037 | 222/633 |
| 6,439,389 B1 * | 8/2002 | Mogil | A45C 3/00 | 206/217 |
| 6,722,679 B2 * | 4/2004 | Englert | B62J 9/005 | 222/610 |
| 6,874,697 B2 * | 4/2005 | Callueng | A61L 2/22 | 222/52 |
| 6,981,613 B1 * | 1/2006 | Kamisugi | A01G 25/145 | 222/105 |
| 7,021,571 B1 * | 4/2006 | Lawson | A47L 11/34 | 239/601 |
| 7,143,958 B1 * | 12/2006 | Dorney | B05B 3/022 | 239/289 |
| 7,243,860 B2 * | 7/2007 | Junkel | A45F 3/16 | 239/302 |
| 7,328,859 B2 * | 2/2008 | Hornsby | B05B 1/3436 | 239/451 |
| 7,347,386 B2 * | 3/2008 | Chen | B05B 9/0861 | 222/143 |
| 7,392,877 B2 * | 7/2008 | Woods, Jr. | F41B 9/00 | 180/311 |
| 7,418,832 B2 * | 9/2008 | Ferrono | B60H 1/00264 | 62/259.4 |
| 7,997,561 B2 * | 8/2011 | Goldmann | F24F 6/12 | 239/11 |
| 8,167,174 B2 * | 5/2012 | Berger | A45F 3/04 | 206/219 |
| 8,662,413 B2 * | 3/2014 | Rotondo | B05B 9/0861 | 239/152 |
| 8,807,455 B2 * | 8/2014 | Havlovitz | B05B 9/0426 | 239/375 |
| 9,488,164 B2 * | 11/2016 | Osborn | E03B 9/20 | |
| 2004/0118940 A1 * | 6/2004 | Lavitt | A01G 25/145 | 239/302 |
| 2005/0077391 A1 * | 4/2005 | Powell | B05B 9/0423 | 239/373 |
| 2006/0086821 A1 * | 4/2006 | Junkel | A45F 3/16 | 239/302 |
| 2006/0144961 A1 * | 7/2006 | DeKeyser | A01C 5/02 | 239/398 |
| 2007/0170280 A1 * | 7/2007 | Ridgeway | B62J 99/00 | 239/146 |
| 2008/0006717 A1 * | 1/2008 | Junkel | A45F 3/16 | 239/333 |
| 2008/0006718 A1 * | 1/2008 | Junkel | A45F 3/16 | 239/333 |
| 2010/0019007 A1 * | 1/2010 | Wagner | A45C 11/20 | 224/148.2 |
| 2011/0121101 A1 * | 5/2011 | Spurlin | B62J 33/00 | 239/289 |
| 2011/0192785 A1 * | 8/2011 | Pritchard | A45F 3/14 | 210/419 |
| 2012/0216755 A1 * | 8/2012 | Collins | A01K 15/02 | 119/712 |
| 2012/0267400 A1 * | 10/2012 | Mohr | B05B 11/001 | 222/331 |
| 2013/0079733 A1 * | 3/2013 | Burt | B05B 7/0012 | 604/290 |
| 2014/0077000 A1 * | 3/2014 | Cooper | B05B 7/2489 | 239/302 |
| 2014/0312142 A1 * | 10/2014 | Lovett | B05B 9/0403 | 239/146 |
| 2014/0361101 A1 * | 12/2014 | Maher | F24F 6/14 | 239/302 |
| 2016/0051997 A1 * | 2/2016 | Seitz | B05B 5/053 | 239/708 |
| 2016/0326765 A1 * | 11/2016 | Barbret | E04H 15/02 | |

\* cited by examiner

PERSONAL COOLING MISTING SYSTEM

CROSS-REFERENCE TO RELATED APPLICATIONS

This disclosure claims priority to U.S. provisional patent application 62/528,283 filed Jul. 3, 2017; the entire contents of which are hereby incorporated by reference.

TECHNICAL FIELD

This disclosure generally relates to cooling systems. More specifically, this disclosure discloses a compact, passive, automatic, easily portable personal cooling misting system designed to provide cooling for a user to combat excessive heat.

BACKGROUND

Individuals often seek ways to stay cool when exposed to elevated ambient temperatures. For example, staying cool and maintaining body temperature is essential in climates of extreme heat, for example, within desert regions and even seasonal environmental regions during peak summer months. Dynamic activities for even a short period of time amid such conditions can be dangerous if the individual fails to maintain body temperature and/or remain hydrated. While the body provides its own natural cooling mechanism through sweating, which at the skin surface provides cooling as the sweat evaporates, the body can become overheated if it is exposed to excessive heat and/or exerted at elevated activity rates for extended periods of time. What is needed is a personal cooling misting system to compliment the body's natural cooling.

While cooling misting systems are known in the art, the state of the art fails to provide for a personal cooling misting system that provides for all of the following; compactness, easy portability by a user, passive, and controllable. A unique solution and disclosed herein is a personal misting system that comprises all of the above features, and the system may be further programmable to accommodate various conditions and users. The system disclosed herein overcomes the above noted downsides to the current state of the art and its disadvantages; particularly non-conventional, bulky and oversized, and/or manually operated misting systems.

SUMMARY

Among various representative embodiments, the present personal cooling misting system may utilize a fluid reservoir dimensioned and contoured to facilitate for a user to wear and carry the fluid reservoir, wherein the fluid reservoir accommodates a volume of a misting fluid. The system further includes an electrically operated pump to pump the misting fluid from the fluid reservoir to a misting head, and the pump is dimensionally configured for proximate positioning and storage to the dimensioned and contoured fluid reservoir, wherein the electrically operated pump may comprise at least one of a piston pump and diaphragm pump. The system may further comprise a plurality of tubing to direct misting fluid from the reservoir to various portions of the system, such as to and from the pump, to a distribution misting head, to a drinking line, to secondary distribution portions, etc. For example, the system comprises feed tubing comprising a first feed tubing end coupled to the fluid reservoir and a second feed tubing end coupled to the electrically operated pump, wherein the feed tubing directs the misting fluid from the reservoir to the electrically operated pump. It may also comprise distributive tubing comprising a first distributive tubing end coupled to the electrically operated pump and a second distributive tubing end coupled to the misting head, wherein the distributive tubing directs the misting fluid from the electrically operated pump to the misting head. Among the various embodiments, the misting head atomizes the misting fluid directed to it, and the misting head can be at least one of, directionally manipulated and variably actuated for use.

The personal cooling misting system further comprises a pump control to control at least one of a pressure, a flow rate, and a misting distribution pattern of the misting fluid through at least one of the feed tubing and distributive tubing, and ultimately to the misting head. Various systems comprise the misting distribution pattern to comprise of at least one of a consistent misting emission, an intermittent misting emission, or various, selectable misting emission rates and/or patterns.

The disclosed system may also comprise a programmable circuit board to facilitate system control to at least one of the electrically operated pump, the pump control, and a key fob, wherein the key fob wirelessly communicates and manipulates at least one of the electrically operated pump, the pump control and/or the programmable circuit board.

The personal cooling misting system may also comprise some, all, or none of the following features such as; the fluid reservoir, which is dimensioned to be received by at least one storage compartment of a backpack, wherein the backpack facilitates wearing the fluid reservoir by the user, a drink line that taps into at least one of the feed tubing and the distributive tubing, and a mechanical securing mechanism coupled to or proximate to the misting head, wherein the mechanical securing mechanism facilitates securing the misting head to a clothing article or an anatomy portion of the use. Additional features may comprise a biometric element attachable to the anatomy portion of the user to communicate to the programmable circuit board at least a physical measurement of the user, and wherein at least one of the electrically operated pump and the pump control operates in response to the physical measurement by the programmable circuit board. Another feature may comprise an environmental sensor to relay at least a temperature to the programmable circuit board to facilitate altering the system's operation in response to changing environmental conditions. Other elements and components may also be incorporated into the system and described in greater detail below.

BRIEF DESCRIPTION OF THE DRAWINGS

A more complete understanding of a personal cooling misting system may be derived by referring to the detailed description and claims when considered in connection with the following illustrative FIGS. In the following FIGS., like reference numbers refer to similar elements and/or steps throughout the FIGS.

The various embodiments and elements in the FIGS. are illustrated for simplicity and clarity, and have not necessarily been rendered according to any particular assembly or sequence. For example, assemblies and/or methods may be performed sequentially, concurrently or in any of a variety of orders.

DETAILED DESCRIPTION

A personal cooling misting system may be described herein in terms of a variety of elements, articles, devices, systems, schematics, or functional block components and/or various method or processing steps. Such elements, articles, devices, systems, schematics, or functional blocks, methods or processing steps may be realized by any number of electrical and/or hardware components that perform specified functions and that may achieve various results. For example, the personal cooling misting system disclosed may employ various misting configurations, pumps, pump controls, pump control boxes, pump control switches, pump housings, user harnesses, liquid reservoirs, tubing, misting heads, backpacks, and other system elements, having any number and variety of configurations that may be understood by those skilled in the art. Moreover, the personal cooling misting system may further employ additional hardware components to provide for the system to operate in a functional, efficient, and aesthetically desirable manner; as well as the electrical components to control the system and/or monitor conditions and/or provide feedback. In addition, the personal cooling misting system may be practiced within any number of environments and may be customizable for a particular cooling use, be it for pleasure, work, sport, governmental use, commercial use, etc. And the personal cooling misting systems that are described are merely representative embodiments and applications of use. Further, the personal cooling misting system may employ any number of conventional techniques for manufacturing, packaging, marketing, selling, distributing, and the like of the personal cooling misting system.

Figure 1:
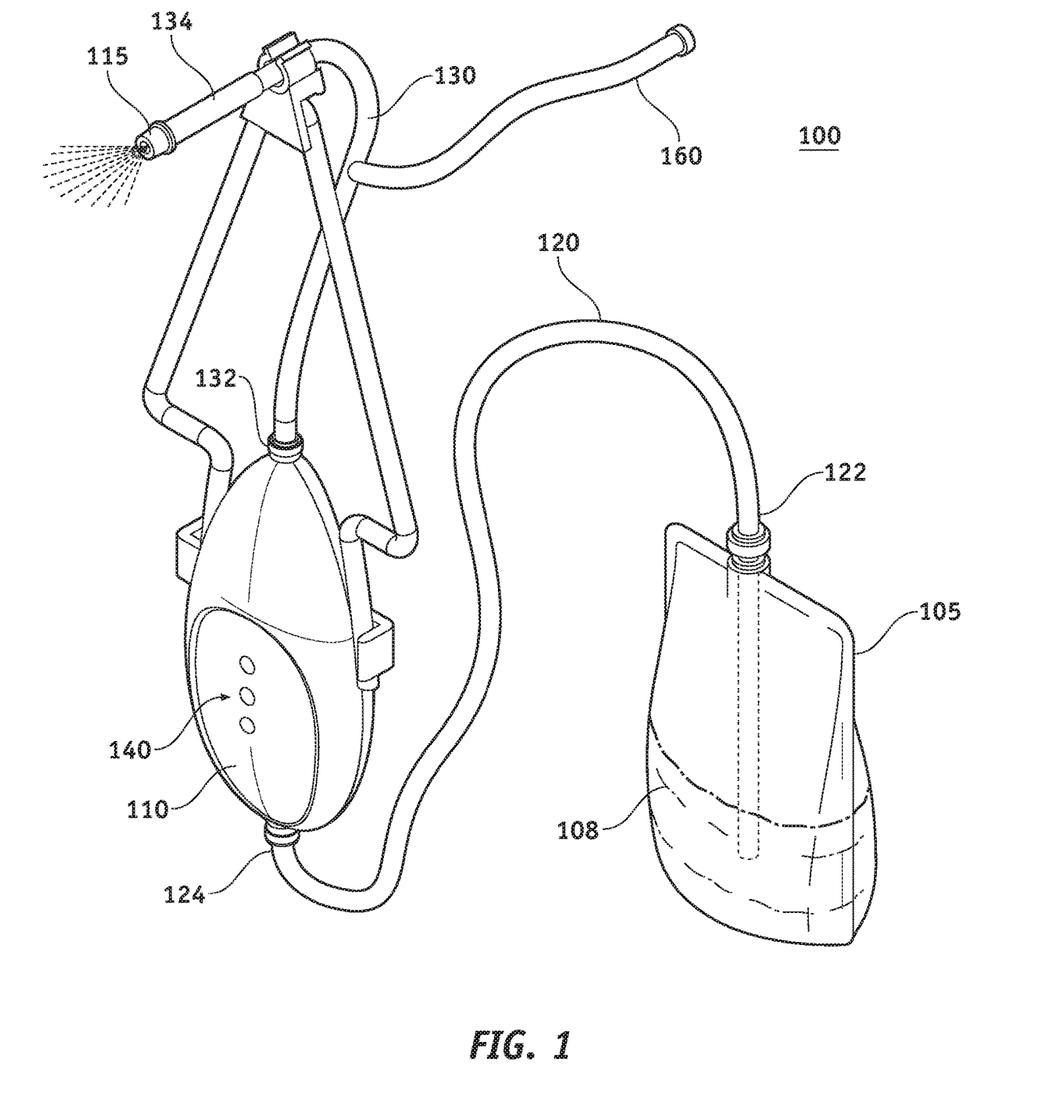
FIG. 1 representatively illustrates an embodiment of a personal cooling misting system.

Various representative embodiments of a personal cooling misting system may be applied to any of various pump style cooling misting system that may be configured and/or adapted for a user. Referring now to FIG. 1, an embodiment of a personal cooling misting system 100 comprises a fluid reservoir 105 dimensioned and contoured to facilitate for a user to wear and carry fluid reservoir 105, wherein fluid reservoir 105 accommodates a volume of a misting fluid 108. System 100 further comprises an electrically operated pump 110 to pump misting fluid 108 from fluid reservoir 105 to a misting head 115, and pump 110 is dimensionally configured for proximate positioning and storage to dimensioned and contoured fluid reservoir 105.

In an embodiment, system 100 comprises feed tubing 120 comprising a first feed tubing end 122 suitably coupled to and/or extending into fluid reservoir 105 and a second feed tubing end 124 suitably coupled to electrically operated pump 110, wherein feed tubing 120 directs misting fluid 108 from reservoir 105 to electrically operated pump 110. In a continuing embodiment, system 100 further comprises distributive tubing 130 comprising a first distributive tubing end 132 suitably coupled to electrically operated pump 110 and a second distributive tubing end 134 suitably coupled to misting head 115, wherein distributive tubing 130 directs misting fluid 108 from electrically operated pump 110 to misting head 115.

Continuing with an embodiment of the personal cooling misting system, system 100 further comprises pump control 140 to control, via electrically operated pump 110, at least one of a pressure, a flow rate, and a misting distribution pattern of misting fluid 108 through at least one of feed tubing 120 and distributive tubing 130. With temporary reference to FIG. 2, system 100 may further comprise a programmable circuit board 250 to facilitate system 100 control either directly or via at least one of electrically operated pump 110, pump control 140, other system 100 components, or perhaps in conjunction with a key fob, such as key fob 270. In an embodiment, key fob 270 wirelessly communicates and manipulates at least one of electrically operated pump 110, pump control 140, programmable circuit board 250, and/or other system 100 components.

Returning now to FIG. 1, fluid reservoir 105 comprises dimensions such that it may be, in a preferred embodiment, received by at least one storage compartment of a backpack (not shown), wherein the backpack facilitates wearing fluid reservoir 105 by the user. As mentioned, fluid reservoir 105 comprises a volume to receive and house misting fluid 108. Fluid reservoir 105 comprises a suitable orifice, known to those in the art, which allows for filling/emptying fluid reservoir 105. Fluid reservoir 105 may comprise a rigid type configuration, a flexible bag type configuration, or any combination thereof. Regardless of configuration, fluid reservoir 105 may comprise materials having requisite durability for repeated use and to withstand shock during use. Fluid reservoir 105 may also comprise proximate sleeves to accept, for example, ice packs to facilitate keeping misting fluid 108 at a desirably low temperature. Fluid reservoir 105 may alternately comprise of a water bottle type configuration, such that a user my easily detach it from other system 100 components to use as a separate water bottle; or system 100 may be operationally configured to benefit from a separate water bottle. Although not the main purpose of the present disclosure, those skilled in the art will further understand that fluid reservoir 105 may comprise any type of vessel that can contain a fluid, such as a large water jug, cooler, vat, tub, and the like that may or may not be easily carried by a user.

In an embodiment, those skilled in the art will understand and appreciate that system 100 may further comprise a drink line, such as drink line 160, that may tap into at least one of feed tubing 120 and/or distributive tubing 130; but preferably into feed tubing 120 as depicted by FIG. 1. In this manner, the user may not only benefit by the topical cooling provided by system 100, but may further benefit by having the ability to ingest fluid 108 to remain internally hydrated; assuming of course that misting fluid 108 comprises a potable fluid suitably for the user. Misting fluid 108 could, in one embodiment, even comprise various electrolytes to provide additional hydration benefits to the user. Those skilled in the art will further understand that an operable valve, such as a Y-type valve/connector may be employed to couple drink line 160 to any of the various disclosed tubing or other system 100 components.

In an embodiment and with continued reference to system 100, system 100 comprises electrically operated pump 110 to pump misting fluid 108 from fluid reservoir 105 to misting head 115, and pump 110 is dimensionally configured for proximate positioning and storage to dimensioned and contoured fluid reservoir 105. In an embodiment, electrically operated pump 110 may preferably comprise at least one of a piston pump and diaphragm pump, although other pump types now known or developed in the future may be employed. As mentioned, pump 110 is dimensionally configured for positioning and storage to fluid reservoir 105. For example and with reference to FIG. 2, pump 110 comprises compact housing portions 211 and 212 to house the pumping elements as well as other system 100 components; such as the electronic circuit board 250 discussed in greater detail below, portions of feed and distribution tubing 120 and 130 that direct misting fluid 108 to and from internal pumping elements, pump controls 140, and perhaps other system 100 components. Pump 110 further comprises an internal electrical source, such as battery 252 to provide the necessary electrical source to drive the operation of pump 110, as well as other system 100 components. In an embodiment, battery 252 may be disposable, but preferably comprises a rechargeable battery source, which may be charged directly or in an embodiment, by a solar powered charging mechanism. In an embodiment, housing portion 212 comprises access panel 216 to accommodate access to battery 252 for replacement, charging, diagnosis, etc. In other embodiments, though, battery 252 may be configured to couple to and provide the power source to pump 110 while positioned at an exterior portion of pump 110's housing, such as an exterior portion of housing portions 211 or 212; and among such embodiments, any exterior placement of battery 252 may be configured for placement in an aesthetically pleasing manner, such as to maintain the contour, smoothness, continuous surface aspect, and other aesthetic characteristic traits of system 100's housing.

Figure 2:
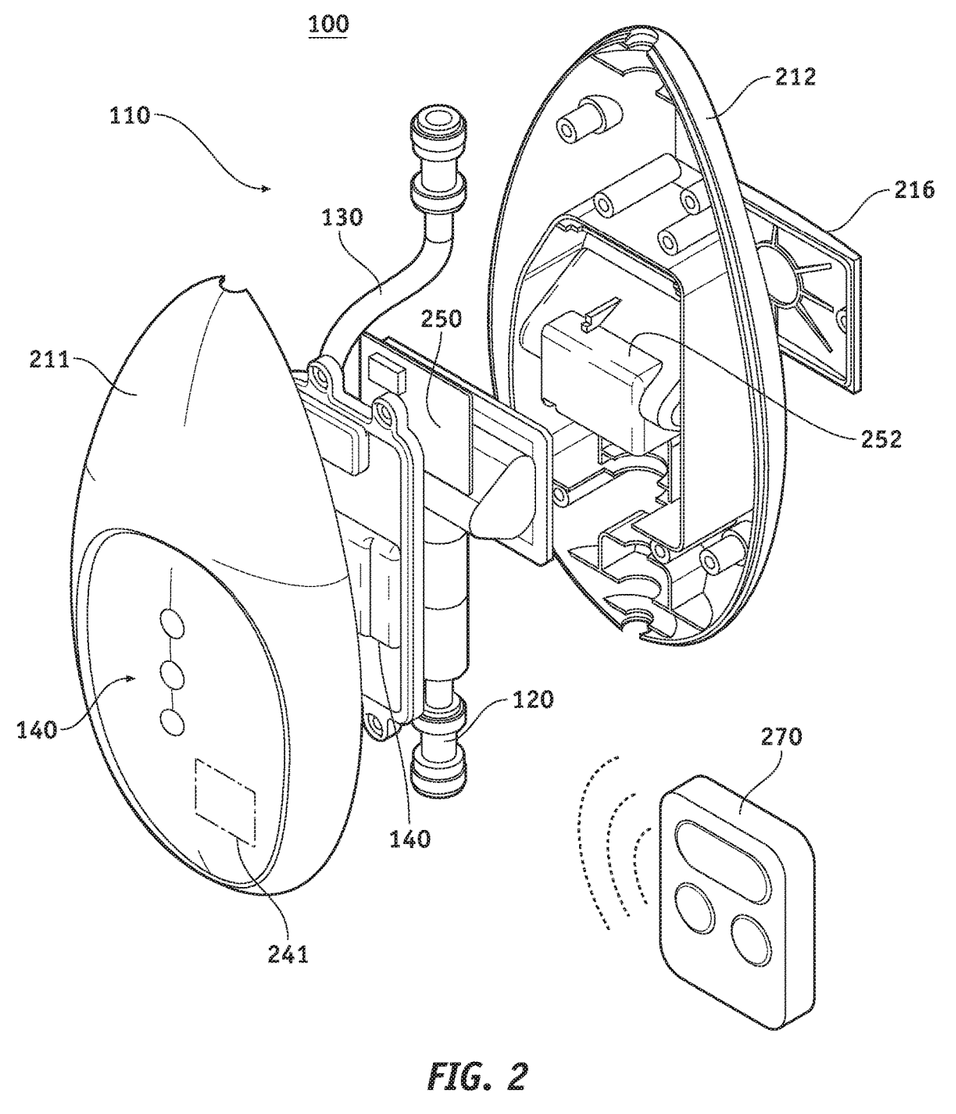
FIG. 2 representatively illustrates an exploded view of a pump from the personal cooling misting system.
Figure 3:
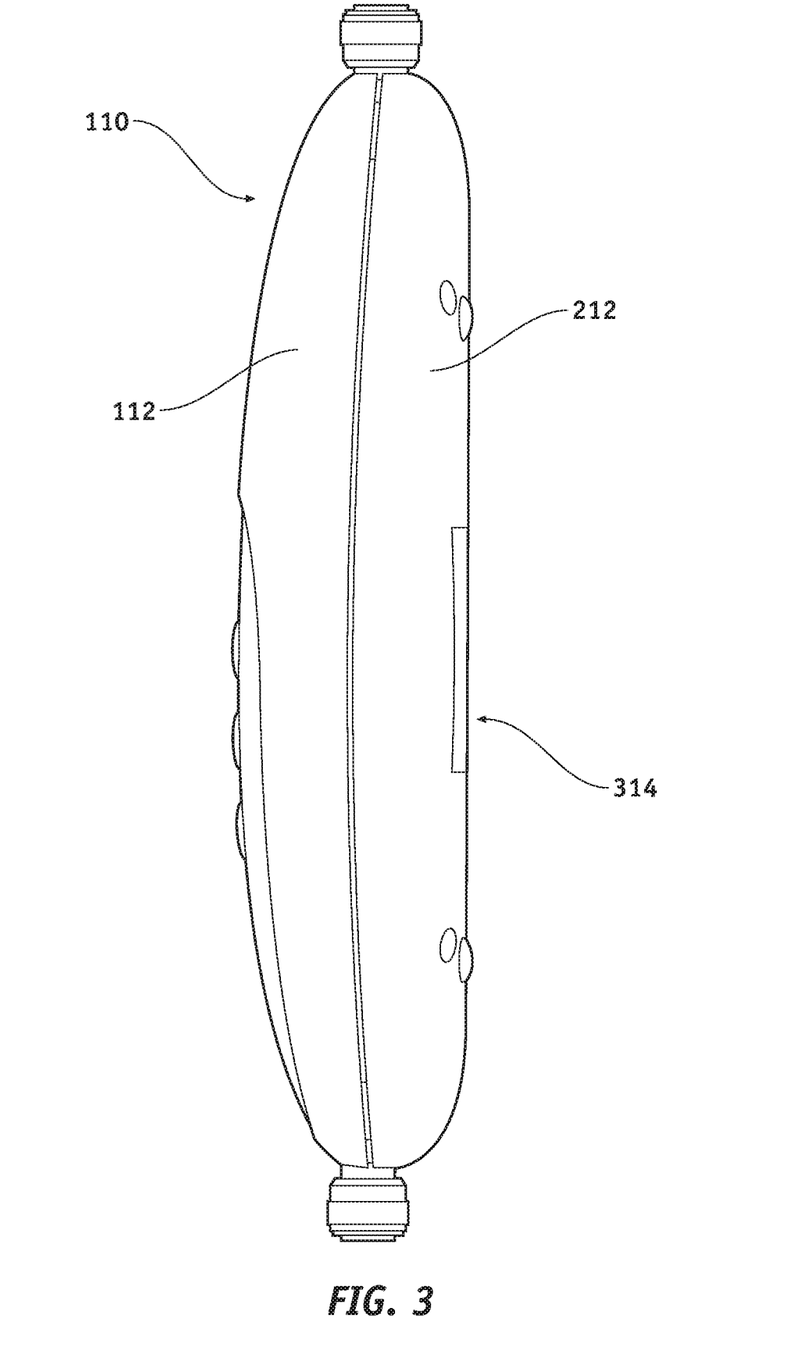
FIG. 3 representatively illustrates a side view of the pump to demonstrate the compact nature of the pump.

It will be further appreciated by those skilled in the art that pump 110 may further comprises pump controls 140 that provide for a user to control pump 110, and in some embodiments pump 110 may comprise a display screen, such as shown by screen 241. To continue with the compact nature of pump 110, it will be appreciated by those skilled in the art that the dimensions of pump 110 are of a compact nature, such that pump 110 is roughly of size to fit in the palm of an average adult. To further appreciate the compact nature of pump 110 and with reference to FIG. 3, a side view of pump 110 demonstrates the narrow configuration of pump 110, and moreover, the relatively planar configuration of the underside of pump 110 as shown by 314, which facilitates pump 110 for placement proximate to fluid reservoir 105 and/or for storage within a backpack or other type of personal toting article. As can be seen by FIGS. 1-3, the external housing portions 211 and 212, in a preferred embodiment, comprise aesthetically pleasing configurations, such as exemplary shown having round contours and relatively smooth surface configurations. Moreover, housing portions 211 and 212 may comprise of a plurality of materials, but in a preferred embodiment comprise of a lightweight material such as lightweight polycarbonate, PVC, and like materials that are durable and may further withstand shock during use.

In an embodiment and disclosed briefly above, system 100 comprises pump controls 140 to control, via electrically operated pump 110, at least one of a pressure, a flow rate, and a misting distribution pattern of misting fluid 108 through at least one of feed tubing 120 and distributive tubing 130. Pump controls 140 may comprise various dial type controls, button type controls, analog controls, digital controls, touch screen controls, as well as pump control feedback mechanisms such as display screens, indicator lights, audio indicators, and others now known or developed in the future. It will be further appreciated by those skilled in the art that pump controls 140 may be directly coupled to electronic circuit board 250, internal pump elements, and other system 100 components.

In an embodiment, system 100 comprises an electronic circuit board, such as electronic circuit board 250. Electronic circuit board may comprise various solid state components to effectuate operation of system 100 in various manners disclosed here or elsewhere in this disclosure. For example, electronic circuit board 250 may be suitably coupled to pump controls, such as pump controls 140, feed and distribution tubing, such as feed tubing 120 and/or distribution tubing 130, misting heads, such as misting head 115, fluid reservoirs, such as fluid reservoir 105, and variety of other system 100 components disclosed herein or developed in the future. The electronic circuit board is preferably shielded from possible interaction and/or contamination by any of misting fluid flowing in proximity to it. In one embodiment, electronic circuit board may be factory programmed to provide for a discrete number of functions to suitably control and/or operate the personal cooling misting system disclosed, or it may be capable of programming by a user either directly or perhaps wirelessly. The electronic circuit board may further be configured to compute and manipulate various inputs, such as by external sensors; and the electronic circuit board may direct other system 100 components in response to such inputs and/or other computations. The electronic circuit board may operate with other system 100 components in a wireless or direct hard wired fashion. Additionally, the electronic circuit board may provide for alerts, be they digital, visual, audio, to be directed to an external environment or user.

In an embodiment and to discuss in greater detail, system 100 comprises misting head 115, wherein misting head 115 atomizes misting fluid 108 directed to it, and may comprise misting heads generally known to those skilled in the art. In an embodiment, misting head 115 can be at least one of, directionally manipulated and variably actuated for use. Variably actuated for use should be understood to mean that misting head 115 may be fully closed, fully open, or set at some discrete or variable position between the fully open and closed position. Moreover, misting head 115 may be configured to provide various misting configurations, such as a conical spray configuration, an elliptical or parabolic spray configuration, a flat spray configuration, etc. In an embodiment, system 100 may comprise for more than a single misting head, but rather multiple misting heads may be employed such that a user may share their personal cooling misting system with a secondary user proximate to them. And system 100 may be configured to accommodate such multiple misting heads, for example, by exploiting multiple distributive tubing coupled to the electrically operated pump.

Among embodiments disclosed, those skilled in the art will appreciate that system 100 may incorporate various ancillary components desirable by various users, as well as to promote safe, efficient, reliable use of system 100. For example, one ancillary component may comprise a misting fluid filter that may be incorporated into system 100. In this manner a user may filter their misting fluid at some point between the fluid reservoir and the misting head; to remove debris, mitigate hard water conditions/distribution, condition the potabililty of the misting fluid, flavor the misting fluid if to be ingested, etc. Another ancillary component, may comprise a pressure relief valve, such that should system 100 encounter an operational condition wherein pump 110 creates an excessive pumping condition without adequate bleed off by any of the other system 100 components, any such elevated pressure condition will be mitigated by relieving pressure through such pressure relief valve. The above are merely two exemplary ancillary components that may be incorporated into system 100, by other ancillary components that may be incorporated into system 100 to further enhance the benefits of system 100 for the user, are contemplated by this disclosure.

In an embodiment and as mentioned above, system 100 comprises feed tubing 120 comprising a first feed tubing end 122 suitably coupled to and/or extending into fluid reservoir 105 and a second feed tubing end 124 suitably coupled to electrically operated pump 110, wherein feed tubing 120 directs misting fluid 108 from reservoir 105 to electrically operated pump 110. System 100 further comprises distributive tubing 130 comprising a first distributive tubing end 132 suitably coupled to electrically operated pump 110 and a second distributive tubing end 134 suitably coupled to misting head 115, wherein distributive tubing 130 directs misting fluid 108 from electrically operated pump 110 to misting head 115. As can be seen with reference to FIG. 2, feed tubing 120 and distributive tubing 130 partially extend into pump 110 to couple to the internal pumping elements. In a preferred embodiment, tubing 120 and 130 comprise a flexible hose type material, but rigid tubing may be employed as well, or a combination of rigid and flexible tubing. Moreover as can be seen throughout the FIGS. tubing 120 and 130 are configured to respectively couple to pump 110 at respective proximate and distal ends of pump 110, however system 100 is not limited in this regard. Depending on various configurations of pump 110, tubing 120 and 130 may couple to pump 110 at any of a number of portions of pump 110, such as, both at a distal portion, both at a proximate portion, at a left, front, back, front side portion, etc of pump 110. In other embodiments, various multiple tubing may be incorporated to accommodate more than a single feed and/or distributive tubing.

In an embodiment, the personal cooling misting system, such as system 100, may further comprise various mechanical securing mechanisms coupled to preferably misting head 115, but also to other system 100 components or the entirety of system 100. The mechanical securing mechanism facilitates securing misting head 115, system 100 components, or the entirety of system 100 directly to or proximate to a clothing article or an anatomy portion of the user. For example, system 100 may comprise a mechanical securing mechanism, such as clips, tabs, screws, snaps, and other like mechanisms to secure a misting head, such as misting head 115, to a bill of a hat, a lapel of a shirt collar, a placket portion of a dress or polo type shirt, and the like. The mechanical securing mechanism may alternately comprise of a Velcro® type wrap, elastic band, and others to secure to or around an anatomical portion of the user, such as an arm, neck, forehead portion, etc. In an alternate embodiment, mechanical securing mechanisms may be specifically configured and employed to secure an exemplary system to an animal, such as a pet dog, a horse, various livestock, or perhaps a young child. Moreover, the system may comprise mechanical securing mechanisms to secure the system to other hardware, mechanical systems, and/or architecture. For example, securing mechanisms may be employed to secure system 100 to an umbrella to create a portable cooling type station, a restaurant patio table, a bicycle, stadium seating, and limitless other examples to facilitate cooling a proximate user.

In an embodiment, a personal cooling misting system, such as system 100, may further comprise at least one biometric element/sensor attachable to the anatomy portion of the user to communicate to preferably electronic circuit board 250, but other system 100 components as well, at least one physical measurement of the user, and wherein at least one of electrically operated pump 110, pump controls 140, or other system 100 components operates in response to the physical measurement. For example, the user may have affixed to a portion of their anatomy one or more biometric elements/sensors that measure; a body surface temperature of the user, other temperatures of the user, a heart rate, a breathing rate, a perspiration condition, and other like biometric conditions.

In an embodiment, a personal cooling misting system, such as system 100, may further comprise an environmental sensor to relay at least a temperature to a programmable circuit board, such as electronic circuit board 250, and/or other system 100 components to facilitate altering system 100's operation in response to changing environmental conditions. For example, the environmental sensor may at random or continuous fashion, detect the temperature of the ambient environment and relay the sensed temperature accordingly to the programmable circuit board or pump controls to alter the pressure, flow rate and/or misting distribution pattern of the system. In this fashion as the user moves from one environment to another, such as from the sun into the shade or vice versa, the system will detect the change via the environmental sensor and adjust the system's operation accordingly. Moreover, the environmental condition may change throughout the day or the sun may experience intermittent cloud cover, thereby further warranting a change of cooling misting to the user. This further accentuates the passive, automatic features of the system.

Those skilled in the art will understand that while elements/sensors may be incorporated into the disclosed system to measure and communicate various external conditions such as environment and biometric as described above, the system is not limited in this regard, and any other elements/sensors that the system may benefit from to maintain a cooling condition by the user, may be employed. For example, a sensor that detects the user transitioning from an outdoor to indoor condition, an area sensor to detect other persons in close proximity, reservoir sensors to alert of reservoir conditions, such as elevated temperature of the reservoir misting fluid and/or fluid levels, as well as other sensors well known to those in the art, but not expressly disclosed herein may be employed. Moreover, various elements/sensors may communicate their measurements in a wireless fashion, or the elements/sensors may be hard-wired and coupled directly to the system.

Continuing with an embodiment of system 100, system 100 provides for various misting distribution patterns, for example a simple misting pattern may comprise at least one of a consistent rate. For example and with reference to FIG. 4, a graphic depiction 480 of misting head fluid distribution as a function of time is shown. Graph line 482 depicts a distribution rate that shows a consistent distribution of misting fluid over time. In a more complex fashion, graph line 484 depicts a distribution rate pattern that is intermittent and varies as a function of time. For example graph line 484 depicts an increasing rate over time as shown by the portion of the pattern at 486 and a decreasing rate as shown by the portion of the pattern at 488. Moreover, those skilled in the art will understand that the rate may comprise a differentiable rate as shown by portion 488 or non-differentiable rate as shown by portion 486. Among various embodiments, almost any number of distribution rates and/or patterns may be employed, as well as a completely random distribution rates and/or patterns. In any event, those skilled in the art will understand that such rates and/or patterns may be programmable and/or controlled by the electronic circuit board, such as electronic circuit board 250, coupled to a suitable input mechanism for a user to select/program such various misting distribution rates and/or patterns. System

Figure 4:
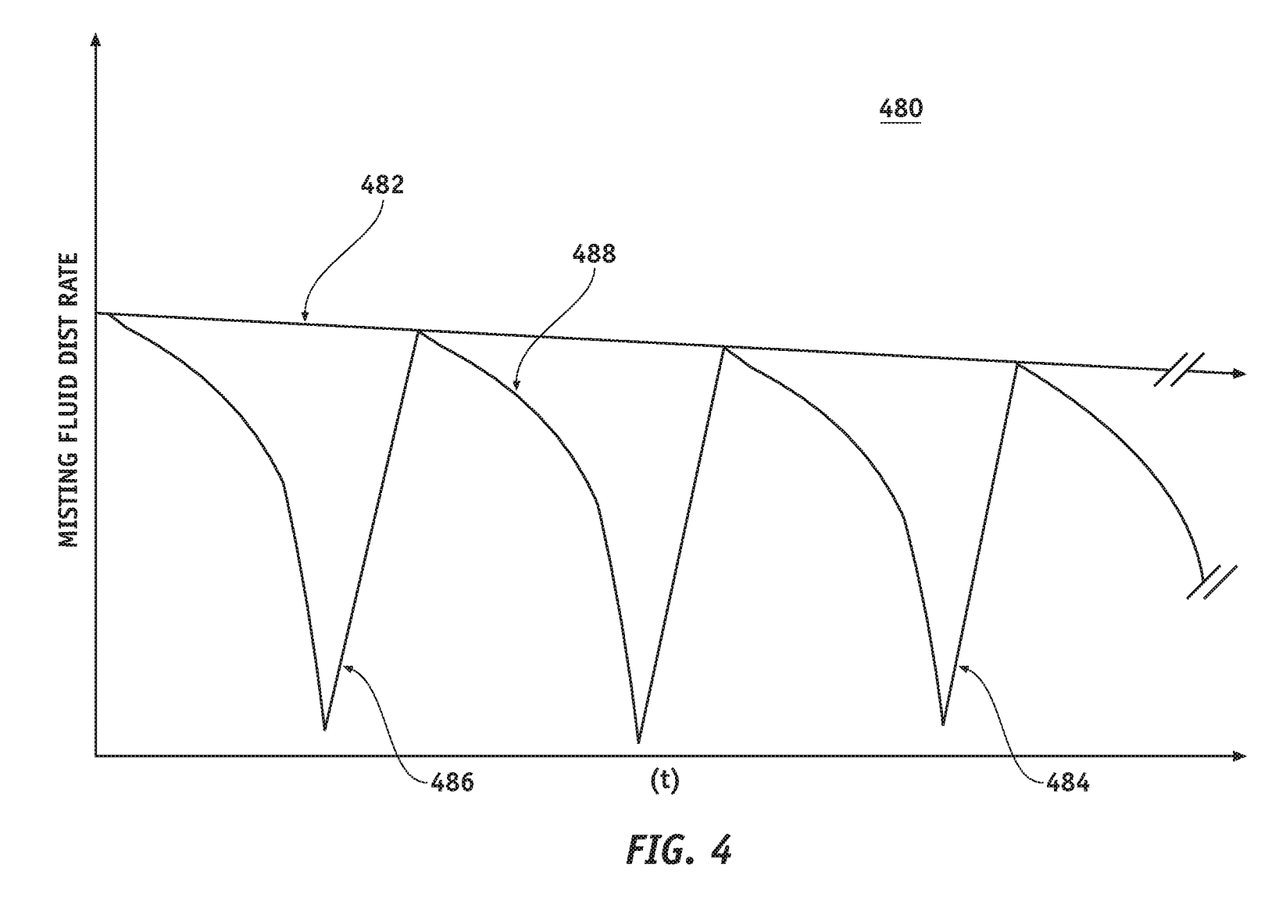
FIG. 4 representatively graphically illustrates various personal cooling misting system distribution rates as a function of time.

100 may further comprise various pump controls, such as pump controls 140, to provide input to electronic circuit board 250 regarding such rates and/or patterns, or to allow a user to select from a discrete number of rates and/or pattern choices. Other system 100 components may provide for selecting and/or operationally providing for a particular misting distribution rates and/or patterns.

It will be appreciated by those skilled in the art that preferred embodiments disclose a personal cooling misting system, but a variety of other configurations and/or applications may be employed without departing from the scope of this disclosure. For example, while this disclosure is generally directed towards a personal cooling misting system for a single user, the present disclosure is not limited in merely that regard, and personal cooling misting systems may be employed for use as noted earlier, but also by a mass of users, for various agricultural and livestock applications, to control the temperature of operating mechanical systems that generate heat, etc.

Those skilled in the art will also understand that while embodiments of a personal cooling misting system have been described, many other embodiments may comprise various other electrical and/or hardware elements not specifically described or as of yet known to those in the art. Furthermore, any of the embodiments described may include some, all, or various combinations of the elements of any of the embodiments described. Finally, while the spirit and scope of this disclosure has focused primarily on the disclosed elements to effectuate the personal cooling misting system, this disclosure contemplates any variety of personal cooling misting configurations for other purposes as noted.

In the foregoing specification, the personal cooling misting system has been described with reference to particular disclosed embodiments. Modifications and changes may be made, however, without departing from the scope of the personal cooling misting system as set forth in the detailed description, FIGS., and claims. The specification and FIGS. are illustrative, rather than restrictive, and any modifications are intended to be included within the personal cooling misting system. Accordingly, the scope of the personal cooling misting system should be determined by the claims and their legal equivalents rather than by merely the embodiments described. For example, the components and/or elements recited in any apparatus, article, device, system, and the like claims may be assembled or otherwise operationally configured in a variety of permutations and are accordingly not limited to only the specific configuration recited in the claims.

Benefits, other advantages and solutions to problems have been described above with regard to particular embodiments; however, any benefit, advantage, solution to problem or any element that may cause any particular benefit, advantage or solution to occur or to become more pronounced are not to be construed as critical, required or essential features or components of any or all the claims.

As used herein, the terms "comprise", "comprises", "comprising", "having", "including", "includes", "is" or any variation thereof, are intended to reference a non-exclusive inclusion, such that a process, method, article, composition, device, system or apparatus that comprises a list of elements does not include only those elements recited, but may also include other elements not expressly listed or inherent to such process, method, article, composition, device, system or apparatus. Other combinations and/or modifications of the above-described structures, arrangements, applications, proportions, elements, materials or components used in the practice of a personal cooling misting system, in addition to those not specifically recited, may be varied or otherwise particularly adapted to specific environments, manufacturing specifications, design parameters or other operating requirements without departing from the general principles of the same.

What is claimed is:

1. A personal cooling misting system adapted for use by an individual user wearing a garment and carrying a backpack, the personal cooling and misting system comprising:
    (a) a fluid reservoir dimensioned and contoured to be retained by at least one storage compartment of said backpack, the fluid reservoir having an interior volume to receive and house at least one fluid, an orifice for filling fluid into the fluid reservoir, a first feed tubing coupling integrally formed with said fluid reservoir;
    (b) an electrically operated pump retained within said backpack and dimensionally configured for proximate positioning and storage to said dimensioned and contoured fluid reservoir;
    (c) said electrically operated pump formed as a compact housing and including an interior chamber surrounded by a first housing portion affixed to a second housing portion, said interior chamber housing an electronic circuit board and an internal source of power, an access panel to accommodate access to the internal source of power, a second feed tubing coupling integrally formed at one end of said electrically operated pump, a first distributive tubing coupling integrally formed with said electrically operated pump and at a location separate from said second feed tubing coupling;
    (d) a first feed tubing having a first feed tubing end coupled to said first feed tubing coupling and in fluid communication with said fluid in said fluid reservoir, the first feed tubing having a second feed tubing end coupled to a second feed tubing coupling and in fluid communication with said electrically operated pump;
    (e) a first distributive tubing having a first distributive tubing end coupled to a first distributive tubing coupling, the first distributive tubing having a second distributive tubing end supported by an attaching member and terminating in and coupled to a misting head;
    (f) a Y-type valve connector coupled to the distributive tubing at a location between the first end of the distributive tubing and the second end of the distributive tubing, the Y-type valve splitting the distributive tubing in two directions, a first direction continuing to the second end of the distributive tubing leading to the misting head and a second direction leading to a drinking line;
    (g) a key fob to wirelessly communicate and send commands to said programmable circuit board having a computer program and to said pump control of said electrically operated pump;
    (h) said key fob commands causing the misting head to atomize the fluid into misting fluid and cause the misting fluid to be directionally manipulated and variably actuated with the misting distribution pattern, with the misting distribution pattern comprising at least one of a constant misting emission, an intermittent misting emission, or various selected misting emission rates, pump controls to control at least one of pressure, flow rate and misting distribution pattern, a feed tubing coupling and a distributive coupling;
    (i) at least one biometric element attachable to an anatomy portion of a user to communicate to the programmable circuit board at least a physical measurement of a user and wherein at least one of the electrically operated pump and the pump control operates in response to the physical measurement by the programmable circuit board; and (j) a mechanical securing mechanism to secure said misting head to said article of clothing causing the misting spray to be sprayed in front of a user's face, neck or head.

2. The personal and cooling misting system in accordance with claim 1, further comprising: said fluid is a liquid.

3. The personal and cooling misting system in accordance with claim 2, further comprising: said liquid is water.

4. The personal and cooling misting system in accordance with claim 1, further comprising: said internal source of power is at least one rechargeable battery.

5. The personal and cooling misting system in accordance with claim 1, further comprising: said electrically operated pump is selected from the group consisting of a piston pump and a diaphragm pump.

6. A personal cooling misting system adapted for use by an individual user wearing a garment and carrying a backpack, the personal cooling and misting system comprising:

(a) a fluid reservoir dimensioned and contoured to be retained by at least one storage compartment of said backpack, the fluid reservoir having an interior volume to receive and house at lest one fluid, an orifice for filling fluid into the fluid reservoir, a first feed tubing coupling integrally formed with said fluid reservoir (b) an electrically operated pump retained within said backpack and dimensionally configured for proximate positioning and storage to said dimensioned and contoured fluid reservoir;

(c) said electrically operated pump formed as a compact housing and including an interior chamber surrounded by a first housing portion affixed to a second housing portion, said interior chamber housing an electronic circuit board and an internal source of power, an access panel to accommodate access to the internal source of power, a second feed tubing coupling integrally formed at one end of said electrically operated pump, a first distributive tubing coupling integrally formed with said electrically operated pump and at a location distal from said second feed tubing coupling;

(d) a first feed tubing having a first feed tubing end coupled to said first feed tubing coupling and in fluid communication with said fluid in said fluid reservoir, the first feed tubing having a second feed tubing end coupled to a second feed tubing coupling and in fluid communication with said electrically operated pump;

(e) a distributive tubing having a first distributive tubing end coupled to a first distributive tubing coupling integrally formed with said electrically operated pump and at a location separate from said second feed tubing coupling, the distributive tubing having a second distributive tubing end supported by an attaching member and terminating in and coupled to a misting head;

(f) at least one biometric element attachable to an anatomy portion of a user to communicate to the programmable circuit board at least a physical measurement of a user and wherein at least one of the electrically operated pump and the pump control operates in response to the physical measurement by the programmable circuit board;

(g) commands sent to said programmable circuit board having a computer program and to said pump control of said electrically operated pump;

(h) said commands causing fluid to travel through the feed tubing from the fluid reservoir to the electrically operated pump, said commands causing distributive fluid to travel through the distributive tubing from the electrically operated pump to the misting head, the commands causing the misting head to atomize the distributive fluid into misting fluid and cause the misting fluid to be directionally manipulated and variably actuated with a misting distribution pattern, with the misting distribution pattern comprising at least one of a constant misting emission, an intermittent misting emission, or various selected misting emission rates, in addition pump controls to control at least one of pressure, flow rate and misting distribution pattern, a feed tubing coupling and a distributive coupling;

(i) at least one biometric element attachable to an anatomy portion of a user to communicate to the programmable circuit board at least a physical measurement of a user and wherein at least one of the electrically operated pump and the pump control operates in response to the physical measurement by the programmable circuit board; and (j) a mechanical securing mechanism to secure said misting head to said article of clothing causing the misting spray to be sprayed in front of a user's face, neck or head.

7. The personal and cooling misting system in accordance with claim 6, further comprising: said fluid is a liquid.

8. The personal and cooling misting system in accordance with claim 7, further comprising: said liquid is water.

9. The personal and cooling misting system in accordance with claim 6, further comprising: said source of power is at least one rechargeable battery.

10. The personal and cooling misting system in accordance with claim 6, further comprising: said electrically operated pump is selected from the group consisting of a piston pump and a diaphragm pump.

11. A personal cooling misting system adapted for use by an individual user wearing a garment, the personal cooling and misting system comprising:

(a) a fluid reservoir dimensioned and contoured to be retained by at least one package worn by the user, the fluid reservoir having an interior volume to receive and house at lest one fluid, a first feed tubing coupling integrally formed with said fluid reservoir (b) an electrically operated pump formed as a compact housing and including an interior chamber surrounded by a first housing portion affixed to a second housing portion, said interior chamber housing an electronic circuit board and an internal source of power, an access panel to accommodate access to the internal source of power, a second feed tubing coupling integrally formed at one end of said electrically operated pump, a first distributive tubing coupling integrally formed with said electrically operated pump and at a location separate from said second feed tubing coupling;

(c) a first feed tubing having a first feed tubing end coupled to said first feed tubing coupling and in fluid communication with said fluid in said fluid reservoir, the first feed tubing having a second feed tubing end coupled to a second feed tubing coupling and in fluid communication with said electrically operated pump;

(d) a distributive tubing having a first distributive tubing end coupled to a first distributive tubing coupling integrally formed with said electrically operated pump and at a location distal to said second feed tubing coupling, the distributive tubing having a second distributive tubing end supported by an attaching member and terminating in and coupled to a misting head;

(e) at least one biometric element attachable to an anatomy portion of a user to communicate to the programmable circuit board at least a physical measurement of a user's face and wherein at least one of the electrically operated pump and the pump control operates in response to the physical measurement by the programmable circuit board;

(f) commands sent to said programmable circuit board having a computer program and to said pump control of said electrically operated pump;

(g) said commands causing fluid to travel through the feed tubing from the fluid reservoir to the electrically operated pump, said commands causing distributive fluid to travel through the distributive tubing from the electrically operated pump to the misting head, the commands causing the misting head to atomize the distributive fluid into misting fluid and cause the misting fluid to be directionally manipulated and variably actuated with a misting distribution pattern, with the misting distribution pattern comprising at least one of a constant misting emission or an intermittent misting emission;

(h) at least one biometric element attachable to an anatomy portion of a user face to communicate to the programmable circuit board at least a physical measurement of a user's face; and (i) a mechanical securing mechanism to secure said misting head to said article of clothing causing the misting spray to be sprayed in front of a user's face;

(j) wherein said misting spray is sprayed in front of a user and timed so that the user walks into the misting spray which hits the user's face, and the user is not drenched with misting fluid poured on top of the user.

12. The personal and cooling misting system in accordance with claim 11, further comprising: said fluid is a liquid.

13. The personal and cooling misting system in accordance with claim 12, further comprising: said liquid is water.

14. The personal and cooling misting system in accordance with claim 11, further comprising: said source of power is at least one rechargeable battery.

15. The personal and cooling misting system in accordance with claim 11, further comprising: said electrically operated pump is selected from the group consisting of a piston pump and a diaphragm pump.

16. The personal and cooling misting system in accordance with claim 11, further comprising: said package is a backpack, the fluid reservoir is dimensioned to be received by at least one storage compartment of the backpack and the electrically operated pump is retained within said backpack and dimensionally configured for proximate positioning and storage to said dimensioned and contoured fluid reservoir.

17. The personal and cooling misting system in accordance with claim 11, further comprising: a drink line that taps into at least one of the feed tubing and the distributive tubing.

18. The personal and cooling misting system in accordance with claim 11, further comprising: a key fob to wirelessly communicate and manipulate a programmable circuit board, wherein the pump control controls operation of the electrically operated pump responsive to a wireless communication from the key fob to the programmable circuit board.

19. The personal and cooling misting system in accordance with claim 11, further comprising: a digital control and a pump control feedback mechanism coupled to the programmable circuit board to facilitate system control to at least one of the electrically operated pump and the pump control wherein the programmable circuit board programmatically commands operation of the electrically operated pump to produce the selected misting distribution pattern upon selection by the user of the misting distribution pattern from a plurality of misting distribution patterns through manipulation of the digital control and the pump control feedback mechanism.

20. The personal and cooling misting system in accordance with claim 11, further comprising: an environmental sensor to relay at least a temperature to the programmable circuit board to facilitate altering the system's operation in response to changing temperature conditions.

* * * * *